US011234680B2

(12) United States Patent
Porvan

(10) Patent No.: US 11,234,680 B2
(45) Date of Patent: Feb. 1, 2022

(54) DIAPER FOR COLLECTING BIOLOGICAL SAMPLES

(71) Applicants: PALMA GROUP SA, Fribourg (CH); Pavlo Porvan, Fribourg (CH)

(72) Inventor: Pavlo Porvan, Fribourg (CH)

(73) Assignee: Palma Group S.A., Fribourg (CH)

( * ) Notice: Subject to any disclaimer, the term of this patent is extended or adjusted under 35 U.S.C. 154(b) by 645 days.

(21) Appl. No.: 16/089,832

(22) PCT Filed: Mar. 31, 2017

(86) PCT No.: PCT/IB2017/051866
§ 371 (c)(1),
(2) Date: Sep. 28, 2018

(87) PCT Pub. No.: WO2017/168388
PCT Pub. Date: Oct. 5, 2017

(65) Prior Publication Data
US 2019/0133560 A1    May 9, 2019

(30) Foreign Application Priority Data

Apr. 1, 2016   (UA) .............................. u 201603399

(51) Int. Cl.
*A61B 10/00* (2006.01)
*A61F 13/49* (2006.01)
(Continued)

(52) U.S. Cl.
CPC ...... *A61B 10/0038* (2013.01); *A61B 5/14507* (2013.01); *A61B 5/14539* (2013.01);
(Continued)

(58) Field of Classification Search
CPC .............. A61B 10/0038; A61B 10/007; A61B 5/14507; A61B 5/14539; A61B 5/14546;
(Continued)

(56) References Cited

U.S. PATENT DOCUMENTS 3,918,433 A     11/1975  Fuisz
4,072,150 A *   2/1978   Glassman ............. A61F 13/493
                                                      604/372
(Continued)

FOREIGN PATENT DOCUMENTS

JP        63124915         8/1988
JP        2004180950       7/2004
(Continued)

OTHER PUBLICATIONS

International Search Report mailed in PCT/IB2017/051866 dated Aug. 31, 2017.

*Primary Examiner* — Michele M Kidwell
(74) *Attorney, Agent, or Firm* — Wissing Miller LLP

(57) ABSTRACT

A diaper for collecting biological samples relates to light industry, and more particularly to a diaper for use in medical examinations and in diagnosing a person's state of health on the basis of an analysis of secretions and/or excreta of the individual. The technical aim of the invention is to create a diaper for the quick and efficient collection of biological samples, the use of which is not restricted by a particular type of indicator substance, and the structural characteristics of which provide for simple, convenient and efficient use. The present diaper (1) for collecting biological samples consists of at least a secretion and/or excreta absorbing base and a detachable absorbing layer (3). The secretion and/or excreta absorbing base of the diaper is provided with at least one through-hole (2). The hole is hermetically sealed on the outside by a sampling element consisting of the detachable absorbing layer and also of a water-impermeable layer (4) and a retaining layer (5).

7 Claims, 2 Drawing Sheets

(51) Int. Cl.
  *A61F 13/15* (2006.01)
  *A61L 15/16* (2006.01)
  *A61B 5/145* (2006.01)
  *A61F 13/84* (2006.01)
  *A61B 5/00* (2006.01)
  *A61F 13/505* (2006.01)

(52) U.S. Cl.
  CPC ........ *A61B 5/14546* (2013.01); *A61B 5/6808* (2013.01); *A61B 10/007* (2013.01); *A61F 13/15* (2013.01); *A61F 13/49* (2013.01); *A61F 13/505* (2013.01); *A61F 13/84* (2013.01); *A61L 15/16* (2013.01); *A61F 2013/8473* (2013.01)

(58) Field of Classification Search
  CPC ...... A61B 5/6808; A61F 13/15; A61F 13/505; A61F 13/84; A61F 2013/8473; A61L 15/16
  See application file for complete search history.

(56) References Cited

U.S. PATENT DOCUMENTS

| | | | | |
|---|---|---|---|---|
| 4,507,121 | A * | 3/1985 | Leung | A61F 13/42 604/361 |
| 4,747,166 | A * | 5/1988 | Kuntz | A61F 5/455 4/144.1 |
| 4,968,312 | A * | 11/1990 | Khan | A61F 13/4915 604/385.13 |
| 5,468,236 | A | 11/1995 | Everhart et al. | |
| 5,573,524 | A * | 11/1996 | Sardo | A61F 13/493 604/358 |
| 5,618,279 | A * | 4/1997 | Pudlo | A61F 5/40 2/403 |
| 5,795,348 | A * | 8/1998 | Roe | A61F 13/505 604/385.19 |
| 5,876,389 | A * | 3/1999 | Bouchard | A61B 10/0045 604/385.16 |
| 6,719,691 | B2 * | 4/2004 | Kritzman | A61B 10/0045 206/305 |
| 7,658,730 | B2 * | 2/2010 | Conley | A61F 5/453 604/350 |
| 8,044,257 | B2 * | 10/2011 | Song | A61F 13/42 604/361 |
| 8,382,734 | B1 * | 2/2013 | Neuenschwander | A61F 13/495 604/385.19 |
| 10,016,318 | B2 * | 7/2018 | Speak | A61F 13/505 |
| 10,408,815 | B2 * | 9/2019 | Kuniavsky | G01N 33/48707 |
| 2002/0067275 | A1 | 6/2002 | Long | |
| 2002/0091364 | A1 * | 7/2002 | Prabhakar | A61F 5/451 604/327 |
| 2005/0070861 | A1 * | 3/2005 | Okabe | A61F 5/455 604/327 |
| 2005/0256467 | A1 * | 11/2005 | Conley | A61F 5/453 604/349 |
| 2007/0185466 | A1 * | 8/2007 | Co | A61F 13/49473 604/349 |
| 2008/0269706 | A1 | 10/2008 | Long et al. | |
| 2008/0269707 | A1 * | 10/2008 | Song | A61B 10/007 604/385.01 |
| 2011/0263952 | A1 * | 10/2011 | Bergman | A61F 13/42 600/309 |
| 2013/0296739 | A1 * | 11/2013 | Schultz | A61B 10/007 600/573 |
| 2015/0051510 | A1 | 2/2015 | Husmark et al. | |
| 2015/0157251 | A1 | 6/2015 | Nelson | |
| 2016/0029957 | A1 | 9/2016 | Faybishenko et al. | |
| 2017/0252014 | A1 * | 9/2017 | Siller Gonzalez | A61F 13/49 |
| 2017/0252233 | A1 * | 9/2017 | Barnhorst | A61F 13/495 |
| 2020/0200739 | A1 * | 6/2020 | Porvan | G01N 21/78 |

FOREIGN PATENT DOCUMENTS

| | | |
|---|---|---|
| JP | 2004212368 | 7/2004 |
| JP | 2011244835 | 12/2011 |
| RU | 2250096 | 4/2005 |
| WO | 9843574 | 10/1998 |
| WO | 2006047815 | 5/2006 |
| WO | 2007073139 | 6/2007 |

* cited by examiner

DIAPER FOR COLLECTING BIOLOGICAL SAMPLES

This application is a 371 of PCT/IB2017/051866 filed on Mar. 31, 2017, published on Oct. 5, 2017 under publication number WO 2017/168388, which claims priority benefits from Ukrainian Patent Application No. U201603399, filed Apr. 1, 2016, the disclosure of which is incorporated herein by reference.

BACKGROUND

Field

The invention relates to light industry and concerns the diaper that can be used in the course of the medical research and diagnostics of human health, based on the analysis of the discharge and/or emptying the human body.

Despite the wide range of diagnostic methods and diagnostic equipment, easy-to-use tools available to detect unwanted changes in your body still remain quite popular. One variant of such tools is the diagnostic diaper that recently widespreads, and as a result, constantly improving, getting more versatility and functionality.

SUMMARY

The diaper, according to the proposed invention, concerns the selection of excrement and/or excreta, for use in diagnosing and for identifying various disorders and pathologies. The proposed invention may find practical use at home, while traveling and in hospitals as auxiliary devices needed for the selection of research samples. Selected samples can later be used for rapid analysis using a variety of test means, and in laboratory conditions using specialized equipment and chemicals.

The term «diaper» presented in invention should be understood as absorbing diapers or pants, designed for both children and adults.

Biological samples should be understood as necessary for analyzing the amount of selected products of vital functions such as urine, feces, and any other secretions from the field covered by diapers, for example, due to inflammation, bleeding, secretion, etc.

The proposed invention is most relevant for use with infants and young children, functionally limited people such as the elderly, bed-ridden due to illness or injury, or those who for other reasons require assistance to be maintained. These categories of persons generally require a systematic medical care. At the same time, studying the health of these people is complicated by the inability or unfitness exercise of independent action for the sampling for analysis, hence the need for the involvement of these procedures by an outside aid and for promoting timeliness of inspection, identifying changes of the health of the body.

One variant for reducing discomfort and for ease of sampling for the analysis was by the way of hygiene products such as diapers, equipped with tools for analysis, such as fillers or inserts that can change the color and/or the intensity of the reaction of liquid components or excrement and/or discharge of the person. Such methods of research, of course, should not be a complete substitute for the research and analysis in specialized laboratories, but they can be very useful to detect changes of the body, especially when staying outside of specialized medical facilities. With these diagnostic and hygiene products, bilirubin, erythrocytes, leukocytes, the presence of nitrites, ketone bodies, protein, urobilinogen, heavy metals such as lead, mercury may be detected to carry out viral diagnostics, to measure pH, etc. These products due to the relative ease of use can be widely used for signal diagnosing the patient without an appropriate professional specialization and a relatively lower cost of efforts and resources.

The basic structure of diapers is the location of indicators or drawing of respective indicator substances on or in the middle of the diaper so that they directly or by means of conducting moisture, contact with faeces fluids and/or secretions of the body. This performance is realized by gluing or by providing zipper indicator strips to the outer layer of the diapers, for the execution of one piece with the surface of nonwoven materials, application by spraying reagents of diaper components, introducing them to the absorbent filler composition.

One example of known analogues is disclosed in the publication of patent application WO 2007073139 dated 28 Jun. 2007. The described diaper comprises a plurality of indicators of urine and faeces that are attached to the inner absorbent substrates and are used to identify proteins and fats, and allow carry out tests for viruses by comparing the color of various indicators. The said diaper is used to detect substances whose content studied in faeces (selection) goes beyond the set normal limit.

The publication to the American patent application US 20020067275 A1 dated 6 Jun. 2002 relates to a known diaper, the inner layer of which has a strip to measure the pH. By contact of the strips with urine resulting in the change of color of the strips, one can determine the acidity of urine, thus identifying infectious processes, including the early stages of development.

U.S. Pat. No. 5,468,236A dated 21 Nov. 1995 discloses an absorbent disposable product which may be a diaper, feminine hygiene, sheets or surgical gowns, etc. including using plural layers of chemically active substances that can change color when in contact with feces. These substances can be located anywhere in the absorbent disposable products where contact is possible with feces. In the shown example, chemically active substances can be applied by spraying, printing, coating, placement of inserts that can be secured zipper gluing, ultrasonic welding, and so on. These reactive compounds can be localized at a certain part or dispersed throughout the product.

All these diapers have significant drawbacks, among which the main one is their low flexibility. In most cases, the above-mentioned diapers, for example, the product according to the US20020067275, are equipped with indicator (indicators) that is (are) able to measure one or more key indicators, which may not be enough for a complete picture of the investigated person and cause a need for other diapers or perform analyzes in the traditional way. However diapers with a wide range of indicators such as, for example, described in WO 2007073139 A and U.S. Pat. No. 5,468,236 A significantly increase their value. Also, not all parameters are measured with the same frequency, but diluting these measurements in the case of diapers with broad set of indicators is impossible because these indicators are used without measurement. Besides the large number of indicators of various chemicals in the diaper, there is the need to streamline their compliance with a specific product in order to prevent their interaction that could lead to a full unfitness of reagents or distortion of the research results. Unlike diapers, which shelf life is long enough, chemical indicators usually have a limited useful life and require specific storage conditions, reducing the shelf life of products for measurement and make it less attractive to retailers. We should note that the presence of various chemical indicators in the composition diaper increases the risk of skin irritations and allergic reactions, especially unacceptable for young children.

The closest analogue of the proposed invention is a diaper for selection of biological samples, disclosed in Invention Patent RU N2250096 C2 dated 20 Apr. 2005. According to one variant of execution of the said closest analogue, is that it contains moisture absorption basis, a hole for the passage of stool and an additional separated absorbent layer. The described diaper allows separate selection of urine and fecal excrement using separated absorbing layers. Its major drawback includes the need for removal of a large part of faeces in the application of the product to reduce the risk of user discomfort, and therefore the product has a too cumbersome and complex structure. The separated diaper layers are located inside the diaper and provide a system of extra layers and a certain order of their location. When filling, the separated layers are removed manually from the diaper through a special niche, which is also a major drawback given the hygienic aspect of this procedure.

Everything mentioned above eliminates the main advantages of known techniques of diapers through which they gained popularity and have become an integral part of the childcare and functionally disabled persons, namely relative affordability, ease of use, speed of removal, hygiene, ability to minimize the used diapers recycling, more.

The objective of the invention is to create a diaper that will allow quick and effective sampling. The use of the diaper is not limited to a certain type of indicator substances and its constructive structure will allow a simple, convenient and efficient use.

The problem is solved by providing a diaper suitable for sampling which absorbs excrement and discharge by an absorbing element. Therefore, according to the invention, in absorbing excrement on diapers, at least one through-hole size sufficient for transmission of the stool and/or discharge beyond the absorptive base of the diaper is made, and is outwardly hermetically sealed with a component for sampling that consists of separated absorbent layer, a waterproof layer and a retaining or holding layer.

Thus, the component for sampling comprises a holding layer to ensure tight connection with the outside of the diaper absorbing layer and separation from the diaper absorbing layer for the purposes of the analysis.

Thus, the holding layer of the sampling element has an adhesive inner surface to allow a tight reconnection with the outer side of the diaper after separation from the absorbing layer for the purposes of the analysis.

Thus, the absorbing layer, water resistant layer and holding layer of the sampling element are made in the form of strips.

Thus, at least one through-hole, closed with the sampling element, is located at the rear bottom of the diaper.

Thus, more than one hole, preferably 3-4 holes with dimensions sufficient for transmission of stool and/or discharge beyond the absorptive diaper base should be made in the base of the absorbing diaper. These holes are hermetically closed by the sampling element.

Thus, the diaper further comprises at least one sampling element that hermetically closes at least one hole, made at the base of the excrement absorbing layer of the diaper, that has a size sufficient for transmission of stool and/or discharge, outside of the absorbing base of the diaper.

The proposed invention has for object to make a selection of biological samples from a diaper performing its basic function without its removal, by using the sampling element.

The sampling element consists of a separable layer used for the analysis of biological material, absorbed by the layer. The biological material may be analysed by any necessary measure for a particular case or by any parameters suitable for this method. The most preferred way is by analysis it using the indicator strips. This method is the most simple and intuitive and does not require specialized training to provide adequate and quick results. Thus, the diaper is designed so as to ensure an easy selection process of the biological samples and to prevent leakage of secretions and faeces and, after sampling to extend its subsequent use for the direct purpose. The contact of secretions and faeces or sampling element with holes is enforced by means of through-holes performed in predictable places of the excrement and/or discharge. It is also possible to perform multiple sampling sites where there is a need to perform a large number of researches. It is also possible to use another sampling element absorbing layer as a control sample for further testing for the analysis.

A preferred but not mandatory option is a variant of making holes and blending of sampling element at the rear bottom of the diaper as the moisture of faeces and/or discharge is uniformly distributed throughout the volume of the absorbent layer and the performance of punctures on the back does not hamper sampling, but will reduce the interest adjustment for the pediatric patients. The size of the holes should be sufficient for a lightweight leakage of stool and/or discharge outside of the diaper and is made in view of the fact that the absorbent layer of the diaper while filling can be expanded and block the holes. At the same time, the holes should not be too large to reduce the possibility of direct contact of the separated absorbing layer of the sampling element with the body. Excessively large size of the holes is not desirable also due to the possible discomfort during withdrawal of the separated absorbing layer and further sealing of the hole with the waterproof and retaining layer of the sampling element. For each type of diapers the optimum size of the holes is determined individually, depending on the properties used for its manufacture, materials. The number of layers of the diaper are preferably in the range of 1-4 mm. The implementation of the water resistant and adhesive layer allows secure retaining of the leakage of the diaper during filling of the separated discharge absorbing layer and allows to continue to keep the emptying and/or selection after disconnecting the absorbing layer. For water resistant layer a conventional polymer film can be used, and for the retaining layer a woven material is used for manufacturing a medical plaster or a polymer material coated with adhesive substance. For such a case, a widely known constructive method shall be applied that is used for sealing packages of wet wipes that provides access to multiple internal contents of the package and provides enough reliable sealing for the duration of use.

The advantage of the proposed invention is that by using the claimed design of the diaper, the user is able to choose the method and the means of the diagnostics of his/her feces and/or secretions of the human body. At the same time the researcher benefits from major advantages inherent to the methods of using of the diagnostic diapers, including the unnecessary surveillance of the emptying point. When using the proposed diaper the user can select the required number of samples for the analysis in compliance with the relative cleanliness and hygiene, the ability to store the diapers and the means of diagnosis in some places, following the storage requirements that are different to the diapers and the means of diagnosis. Along with the use of all the advantages of diapers it is possible to use a larger set of diagnosis than is offered by manufacturers of traditional diagnostic diapers, thereby eliminating the risk of irritant or allergic reactions with possible contacting of the diagnostic tools with the body parts of the investigated person, the amount of possible measurements is limited only by the amount of material that is possible to receive. The appended claims further define the invention.

BRIEF DESCRIPTION OF THE DRAWINGS

The features of the invention is represented in the drawings:
List of graphic figures
FIG. 1 relates to the appearance of the diaper made with partially cut of the sampling element.

DETAILED DESCRIPTION

Figure 1:
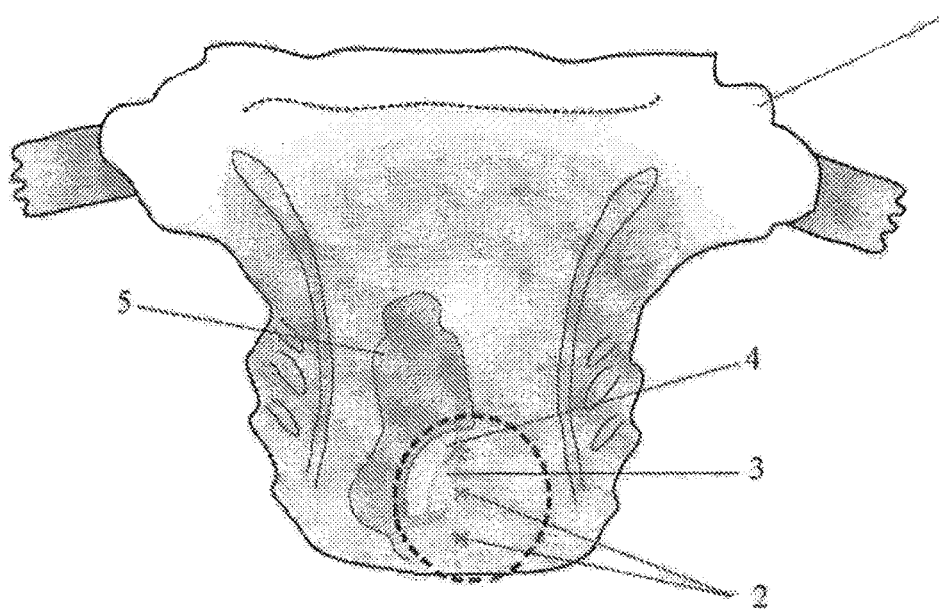
Figure 3:
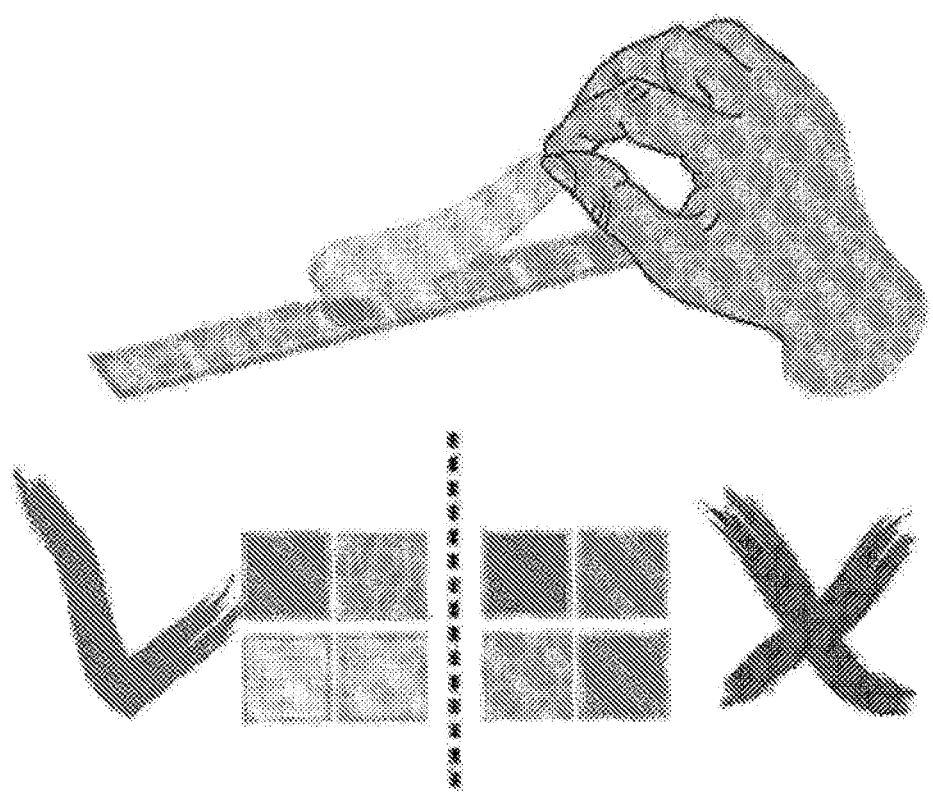
FIG. 3 relates to the image that shows the process of analyzing the biological samples collected by means of the diaper, according to the invention.

FIG. 1 shows the appearance of the diaper 1. In the illustrated example, the element that provides a selection of biological sample is placed on the rear bottom of the diaper. Its dimensions are not regulated and are determined based on the necessary and sufficient quantity of biological material for the analysis. Typically, the length of the absorption band of 0.5 cm is sufficient to test one indicator band, such as it is shown in FIG. 3 and to obtain correct results of the research. For each case and the type of diaper and also the volume of studies to be carried out, the area of the discharge absorbing layer, which will depend on the total area for the sampling element, can be selected according to the situation. For children's diapers the sizes can be somewhat less clear because of the size of the diaper and all of the products of the material. For adult diaper the belt length can vary within a broader range, depending on the tasks and necessity. Based on the fact that in most cases there is a feasibility analysis on several indicators, a detachable absorption layer of size 5×2 cm is sufficient to obtain a sufficient quantity of material for the research.

Figure 2:
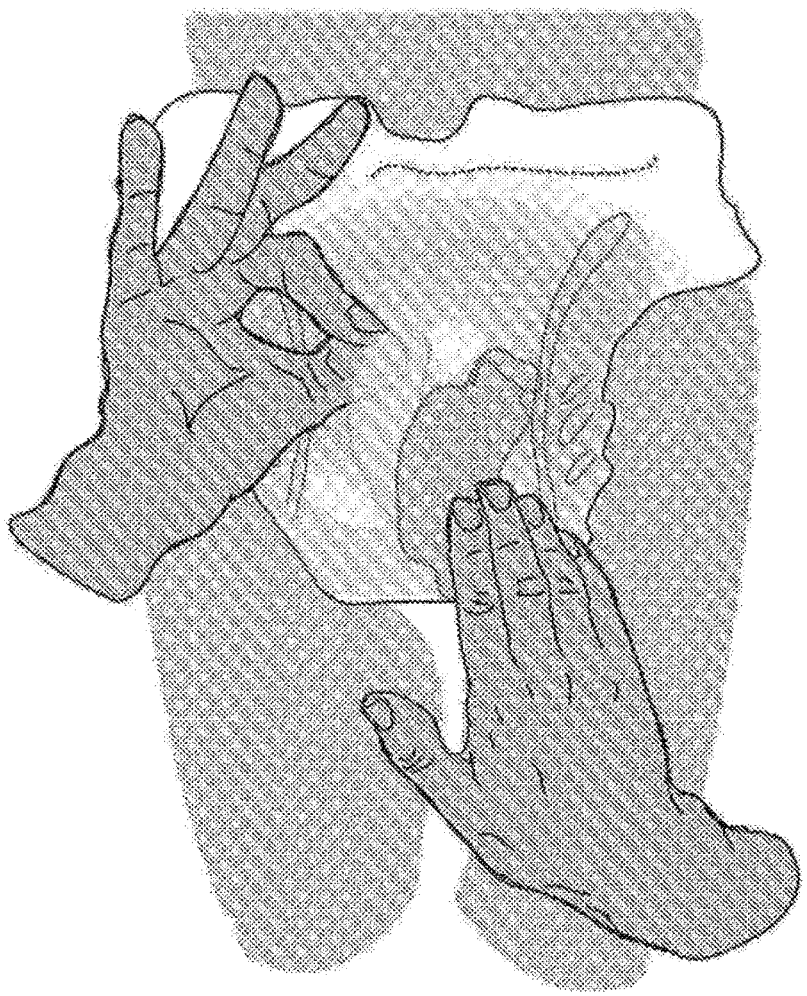
FIG. 2 relates to the image that shows the sampling process using the diaper, according to the invention.

FIG. 1 shows a preferential location of holes 2 for passing of the biological samples outside the diaper. The optimal number of holes is 3-4. The size of the holes, mostly designed to pass urine or moisture from feces, may be slightly enlarged to enable the passage of feces which can partially stick to the separated absorbing layer and may subsequently be used for analysis by the test tools, or directed to the research in the laboratory. The additional holes in this case, may not cause danger of urine discharge after removing of the absorbing layer 3 because the excess of fluid is retained in the holes or around them and will slowly be adsorbed by primary absorbing layer of the diaper. A separated absorbing layer 3 is imposed within the limits of the holes. The main requirement for the separated absorbing layer 3 is the quick collecting of fluid in sufficient quantity. The material of the absorbing layer 3 should be chemically inert to the components of urine and to possible unconventional components, whose appearance is caused by changes in the body. For the most part, the ordinary cotton material is suitable for use with a determined purpose. The separated absorbing layer 3 can be made in the form of a strip of non-woven material or a fabric, depending on what will be the best in the particular case of properties of the strip. To eliminate the further spread of moisture from the separated absorbing layer a water resistant layer 4 shall be imposed onto it. This layer is made of any medically acceptable material, for which the water resistant properties are inherent. The separated absorbing layer 3, the water resistant layer 4 are placed in that the order starting from the outside of the diaper opposite of holes 2, and they are fixed to the outside of the diaper by bonding of the retaining layer 5 using preferably adhesive tape, whose dimensions are larger than the previous layers. As a result of such mounting, the waterproof layer 4 appears completely stuck to the adhesive tape 5 and because the adhesive tape sizes are larger than the previous layers, the waterproof layer forms a tight connection to the outside of the base of the diaper and the waterproof pocket, in which the absorbent layer 3 is placed and after filling can be removed from the pocket without any problems in the manner shown, for example, in FIG. 2. The adhesive tape 5 is made of a sticky coating that can keep their adhesive properties after opening of the pockets and removing of the separated absorbing layer 3. As a result, the holes 2 which retain their property to pass stool, will be blocked as a result of the waterproof strip 4 pressing them with the adhesive tape 5. Over time, the holes in the diaper will be blocked because of the swelling of the absorbent material of the absorption base, thereby minimizing the risk of excrement treatment and/or discharge on the outside when it is filled. This feature provides the ability to further use of the diaper's resource appropriately after the necessary biological sample is selected.

The diaper is used as follows.

The examined person in the time recommended for collecting biological samples should wear a diaper made according to the invention. At a certain frequency the diaper or selecting element shall be verified base on the receipt of the biological samples. In the most preferred case, of selection of biological tests (on urine, moisture from feces or directly feces), the observation requires the immediate opening of the sampling element because the emptying of a sufficient amount for sampling may be determined based on the visual analysis of the diaper, by touch or by smell. If it is necessary to research other secretions caused by inflammation, secretion or blood discharge from the body, a periodic observation of the filling of the separated absorbing layer may be required, if the stool is not as dense as those caused by natural needs. After the filling the separated absorbing layer is judged to be sufficient for studying of the material's quantity, the upper adhesive layer is partially separated by hand from the surface of the outer layer of the diaper until the space so formed will allow to remove the separated absorbing layer from its pocket. This layer shall be removed according to all the research's rules by using specialized tools such as tweezers, hook or manually by using disposable gloves or another suitable method that will provide the required purity accordingly. After selecting the biological samples, these samples can be investigated by any known technical method. Due to the use of the present diaper at home as a simple tool for this purpose, the method of diagnosing shall be applied by using the specific test strips or test reagents. It is possible to use a standardized plate and a set of indicators. The order of the studies can be more intuitively based on the image represented in FIG. 2 and FIG. 3. The absorbing layer after separation from the diaper is applied alternately to the pads located on the tablet. Each pad can be used with a new, band, not used before absorption, to reduce the search error to the minimum. The state of the body shall be determined by the color change of the indicators and according to standard colors attached to the instructions for their use. According to the results of the analysis, a decision shall be made about possible further action for the treatment or prevention, or about returning to a normal mode of healthy living.

An example of a specific implementation.

For research a children's diaper of the largest child-size, labeled by manufacturers for users of 16+ kg was chosen. In the lower part, three through-holes were made, for which sharpened rod with a diameter of 2 mm was used. Opposite the holes, from outside of the diaper a cotton strip with thickness of approximately 3 mm was imposed and from the top of which a plastic layer was placed. A multi-layer construction was secured to the diaper using a medical patch that is larger than the size of the previous layers. To study the practical life of the product, a urine sample from a single urinating in full was selected from the studied person weighing approximately 16 kg according to standard procedures and filled in a specialized container. The selected sample volume was approximately 100 ml. A few selected samples were put into the pipette, which dropped the urine to the test strip designed to determine the pH. The rest of the urine was poured completely on the inside of the diaper as manufactured according to the present invention. By disconnecting the upper layer of plaster, observations on pour seepage of urine was carried out. When checking in 1 minute, by visual and tactile characteristics it was determined that urine leaked to the separated absorbing layer through the main layers of the diaper. This layer was separated from the diaper formed by the space between the upper adhesive layer and the diaper. The separated absorbing layer was removed by hand and applied to test strips for pH, similar to those with which the test was performed by dripping via the pipette. The moisture absorbed by the strip was enough to change the color of the test strip, applied at the absorption bands and test strips to each other. Comparing the results of the testing performed by dripping directly on the test strip and using samples collected by means of the diaper showed similar results, which confirmed the suitability of the proposed invention for selection of biological samples and the ability to use them for diagnostic purposes. The practical use of the diaper design directly on the child proved its reliability with regard to the leaks, in the process of filling and after removal of the absorption bands from the pocket holding it. The baby did not show any sign of inconvenience or discomfort of wearing such a diaper. Thus the practical suitability of the proposed diaper was fully confirmed to select biological samples while preserving their basic functions.

The proposed invention is not limited to the illustrated embodiment and can be used in other specific forms without losing the overall trends and essential attributes. Therefore, the described embodiment should be considered in all respects only as illustrative and not as limiting the amount of the invention. Any changes that may be proposed as equivalent within formula should be considered as being included in it.

The invention claimed is:

1. A diaper for selection of biological samples comprising at least one absorbing excrement base and a separated absorbing layer, wherein a plurality of through-holes are provided in the at least one base of the diaper, wherein the plurality of through-holes are of size sufficient for passing stool and/or discharge beyond the at least one absorbing base of the diaper while the plurality of through-holes are hermetically closed by a sampling element, wherein the sampling element is externally connected to the diaper to seal the plurality of through-holes and wherein the sampling element comprises the separated absorbing layer, a waterproof layer and a retaining layer.

2. The diaper according to claim 1, wherein the layer containing the sampling element is reconnectable to the diaper to ensure a tight connection with an external part of the diaper after separation of the absorbing layer for needs of analysis.

3. The diaper according to claim 1 wherein the retaining layer has an adhesive inner surface to allow tight reconnection of the sampling element with an external part of the diaper after separation of the separated absorbing layer for needs of analysis.

4. The diaper according to claim 1 wherein the absorbing layer, the waterproof layer and the retaining layer constitute the sampling element in the form of a strip.

5. The diaper according to claim 1 wherein at least one of the plurality of through-holes, hermetically closed with the sampling element, is located at a rear bottom of the diaper.

6. The diaper according to claim 1, further comprising one additional hole, wherein the sampling element hermetically closes the at least one additional hole in the absorbing base of the diaper, and wherein the additional hole has a size sufficient for passing stool and/or discharge outside the absorbing base of the diaper.

7. The diaper of claim 1, wherein the plurality of through-holes comprises 3 or 4 through-holes.

* * * * *